United States Patent
Phillips et al.

(10) Patent No.: US 11,466,320 B2
(45) Date of Patent: Oct. 11, 2022

(54) MULTI-SEQUENCE CAPTURE SYSTEM

(71) Applicant: University of Utah Research Foundation, Salt Lake City, UT (US)

(72) Inventors: John D. Phillips, Salt Lake City, UT (US); Jennifer M. Heemstra, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 320 days.

(21) Appl. No.: 16/413,563

(22) Filed: May 15, 2019

(65) Prior Publication Data

US 2020/0071756 A1    Mar. 5, 2020

Related U.S. Application Data

(63) Continuation of application No. 15/650,832, filed on Jul. 14, 2017, now Pat. No. 10,465,242.

(60) Provisional application No. 62/362,288, filed on Jul. 14, 2016, provisional application No. 62/393,592, filed on Sep. 12, 2016, provisional application No. 62/704,006, filed on May 15, 2018.

(51) Int. Cl.
*C12Q 1/6874* (2018.01)
*C12Q 1/6806* (2018.01)
*C12Q 1/6876* (2018.01)
*C12Q 1/6816* (2018.01)

(52) U.S. Cl.
CPC ........ *C12Q 1/6874* (2013.01); *C12Q 1/6806* (2013.01); *C12Q 1/6816* (2013.01); *C12Q 1/6876* (2013.01)

(58) Field of Classification Search
None
See application file for complete search history.

(56) References Cited

U.S. PATENT DOCUMENTS 6,743,905 B2   6/2004  Woo et al.
7,074,569 B2   7/2006  Woo et al.
(Continued)

OTHER PUBLICATIONS

Iwai et al.; "5'-Levulinyl and 2'-tetrahydrofuranyl protection for the synthesis of oligoribonucleotides by the phosphoramidite approach"; Nucleic Acids Research; (Oct. 25, 1988); pp. 9443-9456; vol. 16, No. 20; Japan.
(Continued)

*Primary Examiner* — Kaijiang Zhang
(74) *Attorney, Agent, or Firm* — Todd B. Alder

(57) ABSTRACT

Branching phosphoramidite monomers and molecules having comb-like structures are disclosed and described. A branching phosphoramidite monomer having the structure

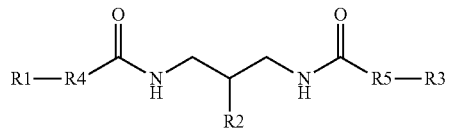

is provided wherein R4 and R5 are independently —(O—$CH_2$—$CH_2$—)$_n$ where n is 1-5 or —O—($CH_2$—)$_n$ where n is 1-10, and R1, R2, and R3 are each one of dimethoxytrityl (DMT)—O—, levulinyl (Lev)—O—, and a phosphoramidite.

6 Claims, 7 Drawing Sheets
Specification includes a Sequence Listing.

(56) References Cited

U.S. PATENT DOCUMENTS

| | | | |
|---|---|---|---|
| 7,211,654 | B2 | 5/2007 | Gao et al. |
| 7,553,958 | B2 | 6/2009 | Gao et al. |
| 7,807,807 | B2 | 10/2010 | Gao et al. |
| 7,897,338 | B2 | 3/2011 | Woo et al. |
| 7,928,207 | B2 | 4/2011 | Bodepudi et al. |
| 8,053,187 | B2 | 11/2011 | Gao et al. |
| 8,138,330 | B2 | 3/2012 | Leuck et al. |
| 8,461,317 | B2 | 6/2013 | Gao et al. |
| 8,481,698 | B2 | 7/2013 | Lieberman et al. |
| 9,303,055 | B2 | 4/2016 | Gao et al. |
| 2007/0026434 | A1 | 2/2007 | Woo et al. |
| 2007/0219361 | A1 | 9/2007 | Bodepudi et al. |
| 2008/0269068 | A1 | 10/2008 | Church et al. |
| 2011/0160082 | A1 | 6/2011 | Woo et al. |
| 2013/0274117 | A1 | 10/2013 | Church et al. |
| 2015/0031555 | A1 | 1/2015 | Johnson et al. |
| 2015/0154352 | A1 | 6/2015 | Johnson et al. |
| 2015/0299695 | A1* | 10/2015 | Uhlmann et al. ......... A61P 9/00 435/375 |
| 2015/0344871 | A1 | 12/2015 | Johnson et al. |
| 2016/0122753 | A1 | 5/2016 | Mikkelsen et al. |

OTHER PUBLICATIONS

Katajisto et al.; "Solid-Phase Synthesis of Oligonucleotide Glycoconjugates Bearing Three Different Glycosyl Groups: Orthogonally Protected Bis(hydroxymethyl)- N,N'-bis(3-hydroxypropyl)malondiamide Phosphoramidite as Key Building Block"; The Journal of Organic Chemistry; (Oct. 29, 2004); pp. 7609-7615; vol. 69, No. 22; American Chemical Society; <doi: 10.1021/jo048984o >.

Katolik et al.; "Regiospecific Solid-Phase Synthesis of Branched Oligoribonucleotides That Mimic Intronic Lariat RNA Intermediates"; The Journal of Organic Chemistry; (2014); pp. 963-975; vol. 79, No. 3; ACS Publications.

Lackey et al.; "Acetal Levulinyl Ester (ALE) Groups for 2'-Hydroxyl Protection of Ribonucleosides in the Synthesis of Oligoribonucleotides on Glass and Microarrays"; Journal of American Chemical Society; (Jun. 24, 2009); pp. 8496-8502; vol. 131, No. 24; <doi: 10.1021/ja9002074 >.

Lackey et al.; "The Acetal Levulinyl ester (ALE) group for the 2'-hydroxyl protection of ribonucleosides and the synthesis of oligoribonucleotides"; Nucleic Acids Symposium Series; (Sep. 8, 2008); pp. 35-36; No. 52; Oxford University Press <doi: 10.1093/nass/nrn018 >.

Macosko et al.; "Drop-Seq Laboratory Protocol"; Harvard Medical School; (Dec. 28, 2015); 20 pages; Version 3.1, Steve McCarroll's lab <URL: www.mccarrolllab.com/dropseq >.

Macosko et al.; "Highly Parallel Genome-wide Expression Profiling of Individual Cells Using Nanoliter Droplets"; Cell; (May 21, 2015); pp. 1202-1214; vol. 161, Issue 5, Elsevier Inc.

Reddy et al.; "Facile Access to 5'-S-(4,4'-Dimethoxytrityl)-2',5'-Dideoxyribonucleosides via Stable Disulfide Intermediates"; Current Protocols in Nucleic Acid Chemistry; (Sep. 1, 2015); pp. 1.34.1-1.34; vol. 62; <doi: 10.1002/0471142700.nc0134s62 >.

Ueno et al.; "Synthesis of 3'-3'-linked oligonucleotides branched by a pentaerythritol linker and the thermal stabilities of the triplexes with single-stranded DNA or RNA"; Bioconjugate Chemistry; May-Jun. 2003); pp. 684-689; vol. 14, No. 3; American Chemical Society; <doi: 10.1021/bc020059q >.

* cited by examiner

MULTI-SEQUENCE CAPTURE SYSTEM

CROSS-REFERENCE TO RELATED APPLICATIONS

This application is a continuation-in-part of U.S. patent application Ser. No. 15/650,832 filed on Jul. 14, 2017, filed on May 15, 2018, which claims the benefit of U.S. Provisional Patent Application No. 62/362,288, filed on Jul. 14, 2016, and U.S. Provisional Patent Application No. 62/393,592, filed on Sep. 12, 2016, both of which are incorporated herein by reference.

GOVERNMENT LICENSE RIGHTS

This invention was made with government support under grant numbers DK020503 and DK090257, awarded by the National Institutes of Health, and under grant numbers 1308364 and 1608561, awarded by the National Science Foundation. The government has certain rights in the invention.

BACKGROUND

Branched DNAs (bDNAs) having comb-like structures have found wide utility in molecular diagnostics and DNA nanotechnology. bDNAs can be generated either by designing and assembling linear DNA molecules into rigid non-covalent structures or by using an orthogonally protected branching unit to synthesize covalently linked structures. Despite advantages of the covalently linked structures, use of this motif has been hampered by the challenging synthesis of appropriately protected branching monomers.

BRIEF DESCRIPTION OF THE DRAWINGS

For a fuller understanding of the nature and advantage of the present disclosure, reference is being made to the following detailed description of embodiments and in connection with the accompanying drawings, in which.

DESCRIPTION OF EMBODIMENTS

Figure 1:
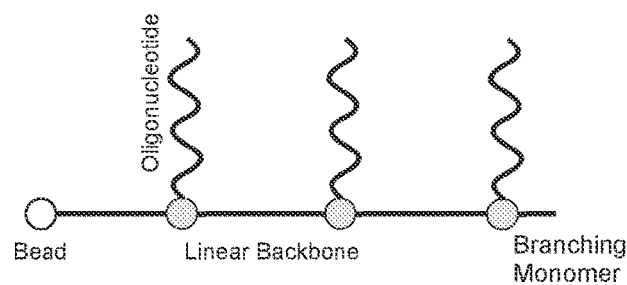
FIG. 1 illustrates a branching phosphoramidite molecule having orthogonal oligonucleotide sidechains arranged in a comb-like structure in accordance with an example of the present disclosure.

Although the following detailed description contains many specifics for the purpose of illustration, a person of ordinary skill in the art will appreciate that many variations and alterations to the following details can be made and are considered included herein. Accordingly, the following embodiments are set forth without any loss of generality to, and without imposing limitations upon, any claims set forth. It is also to be understood that the terminology used herein is for describing particular embodiments only and is not intended to be limiting. Unless defined otherwise, all technical and scientific terms used herein have the same meaning as commonly understood by one of ordinary skill in the art to which this disclosure belongs. Also, the same reference numerals appearing in different drawings represent the same or similar element. Numbers provided in flow charts, processes, and the like, are provided for clarity in illustrating steps and operations, and do not necessarily indicate a particular order or sequence.

Furthermore, the described features, structures, techniques, or characteristics can be combined in any suitable manner in one or more embodiments. In the following description, numerous specific details are provided in order to provide a thorough understanding of various embodiments. One skilled in the relevant art will recognize, however, that such detailed embodiments do not limit the overall concepts articulated herein but are merely representative thereof. One skilled in the relevant art will also recognize that the technology can be practiced without one or more of the specific details, or with other methods, components, etc. In other instances, well-known structures, materials, or operations may not be shown or described in detail to avoid obscuring aspects of the disclosure.

In this application, "comprises," "comprising," "containing" and "having" and the like can have the meaning ascribed to them in U.S. Patent law and can mean "includes," "including," and the like, and are generally interpreted to be open ended terms. The terms "consisting of" or "consists of" are closed terms, and include only the components, structures, steps, or the like specifically listed in conjunction with such terms, as well as that which is in accordance with U.S. Patent law. "Consisting essentially of" or "consists essentially of" have the meaning generally ascribed to them by U.S. Patent law. In particular, such terms are generally closed terms, with the exception of allowing inclusion of additional items, materials, components, steps, or elements, that do not materially affect the basic and novel characteristics or function of the item(s) used in connection therewith. For example, trace elements present in a composition, but not affecting the compositions nature or characteristics would be permissible if present under the "consisting essentially of" language, even though not expressly recited in a list of items following such terminology. When using an open-ended term in this written description, like "comprising" or "including," it is understood that direct support should be afforded also to "consisting essentially of" language as well as "consisting of" language as if stated explicitly and vice versa.

As used herein, the term "substantially" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking the nearness of completion will be so as to have the same overall result as if absolute and total completion were obtained. The use of "substantially" is equally applicable when used in a negative connotation to refer to the complete or near complete lack of an action, characteristic, property, state, structure, item, or result. For example, a composition that is "substantially free of" particles would either completely lack particles, or so nearly completely lack particles that the effect would be the same as if it completely lacked particles. In other words, a composition that is "substantially free of" an ingredient or element may still actually contain such item as long as there is no measurable effect thereof.

As used herein, the term "about" is used to provide flexibility to a given term, metric, value, range endpoint, or the like. The degree of flexibility for a particular variable can be readily determined by one skilled in the art. However, unless otherwise expressed, the term "about" generally provides flexibility of less than 1%, and in some cases less than 0.01%. It is to be understood that, even when the term "about" is used in the present specification in connection with a specific numerical value, support for the exact numerical value recited apart from the "about" terminology is also provided.

As used herein, a plurality of items, compositional elements, materials, and/or the like, may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary. Additionally, it is intended that support is provided by such lists for the list as a whole, an individual item from the list, and any selection or grouping of items from the list.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc., as well as 1, 1.5, 2, 2.3, 3, 3.8, 4, 4.6, 5, and 5.1 individually. This same principle applies to ranges reciting only one numerical value as a minimum or a maximum. Furthermore, such an interpretation should apply regardless of the breadth of the range or the characteristics being described.

Reference throughout this specification to "an example" means that a particular feature, structure, or characteristic described in connection with the example is included in at least one embodiment. Thus, appearances of phrases including "an example" or "an embodiment" in various places throughout this specification are not necessarily all referring to the same example or embodiment.

Example Embodiments

An initial overview is provided below, and specific embodiments are then described in further detail. This initial summary is intended to aid readers in understanding the technology more quickly but is not intended to identify key or essential technological features, nor is it intended to limit the scope of the claimed subject matter.

Comb polymers offer unique properties and capabilities that are, at least in part, due to oligomer sidechains arrayed in parallel along a linear backbone. Similarly, branched oligonucleotides (b-Oligos), such as branched deoxyribonucleic acid (DNA; bDNA), for example, can be constructed such that a series of oligonucleotides are arrayed along a synthetic or oligonucleotide backbone. The capabilities of b-Oligos have been harnessed for the construction of diverse and complex DNA self-assembled structures, driving promising new applications in fields including molecular diagnostics, biosensors, next generation sequencing (NGS), DNA computing, and the like. Two different strategies have generally been employed to generate bDNAs, for example: (1) non-covalent assembly of linear oligonucleotides to generate a double-stranded DNA backbone having overhanging single-stranded DNA tails; and (2) synthesis of a backbone having covalently attached single-stranded DNA units using a branching monomer. The covalent approach offers various advantages, such as higher stability, greater control over branching angle, decreased total quantity of DNA required, and the like. Despite these advantages, however, the covalent approach to bDNA construction has not found wide use, likely due to the lack of conveniently available branching monomers having orthogonal protecting groups. Orthogonally protected branching phosphoramidites have been synthesized based upon cytosine or adenosine scaffolds, and subsequently used for synthesis of comb-like or lariat oligonucleotide structures. These structures have been subsequently applied as signal amplifiers for the quantification of nucleic acids or to monitor lariat debranching enzyme activity, to name a few. However, synthesis of these nucleoside-based branching units having orthogonal protecting groups involves complex and lengthy synthetic procedures, hindering their widespread use.

Furthermore, while the branching monomers used in covalent approaches enable the synthesis of dendrimeric and comb-like structures, such branching monomers have identical protecting groups on sidechains that result in branching molecules with sidechains having identical oligonucleotide sequences due to the inability to selectively deprotect individual sidechains for independent synthesis. Creating comb-like structures having orthogonally arranged sidechains capable of selective sidechain deprotection for oligonucleotide synthesis has proven difficult, particularly given the sensitivity of oligonucleotide molecules to most deprotection chemistries.

Figure 2A:
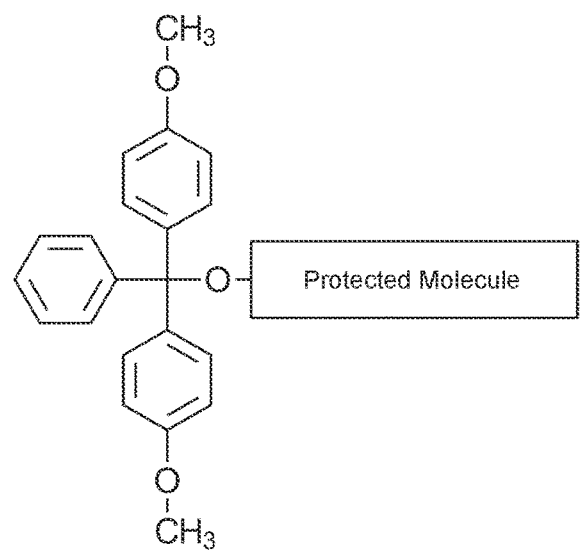
FIG. 2A illustrates a dimethoxytrityl (DMT) protecting group coupled to a protected molecule in accordance with an example of the present disclosure.
Figure 2B:
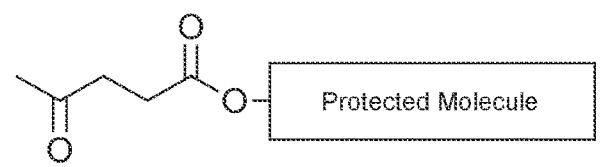
FIG. 2B illustrates a levuniyl (Lev) protecting group coupled to a protected molecule in accordance with an example of the present disclosure.

The present disclosure provides techniques for solving such problems that involve the use of branching phosphoramidite monomers and molecules having dimethoxytrityl (DMT) and levuniyl (Lev) protecting groups. Examples of DMT and Lev are shown In FIG. 2. Such DMT and Lev protecting groups can each be selectively removed under conditions that are compatible with ribonucleic acid (RNA) and DNA synthesis. This protecting group strategy can thus be utilized to synthesize an asymmetrically-protected branching phosphoramidite, which can then be to the creation of comb-like b-Oligo molecules having multiple independently synthesizable oligonucleotide sidechains. A very generalized and nonlimiting example of a comb-like b-Oligo molecule is shown in FIG. 1 having a linear backbone extending from a solid substrate, such as a bead. The linear backbone includes a number of branching phosphoramidite monomers, each with an independently synthesizable oligonucleotide extending orthogonally therefrom.

DMT and Lev protecting groups thus allow the selective deprotection of reactive groups on a branching phosphoramidite monomer to facilitate protection during branching phosphoramidite monomer incorporation into the growing linear phosphoramidite backbone and the subsequent synthesis of an oligonucleotide (or other molecule of use) without affecting other sidechain moieties. Various branching phosphoramidite monomer structures are contemplated and any such structure having a phosphoramidite group and DMT and Lev protected branches that is capable of forming a linear phosphoramidite backbone with independently synthesizable sidechains is considered to be within the present scope.

In one example, a branching phosphoramidite monomer can have the structure

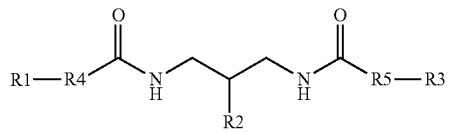

where R4 can be a polyethylene glycol (PEG) such as —(O—CH$_2$—CH$_2$—)$_n$ where n is 1-5, an alkyl such as —O—(CH$_2$—)$_n$ where n is 1-10, or similar. R5 can be, in some cases independently of R4, a PEG such as —(O—CH$_2$—CH$_2$—)$_n$ where n is 1-5, an alkyl such as —O—(CH$_2$—)$_n$ where n is 1-10, or similar. Furthermore, R1, R2, and R3 can each one of DMT, Lev, and a phosphoramidite.

In another example, a branching phosphoramidite monomer can have the structure

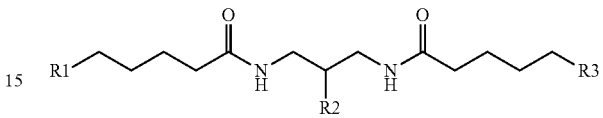

where, R1, R2, and R3 can each one of DMT, Lev, and a phosphoramidite. In one specific example, R2 can be the phosphoramidite.

In another example, a branching phosphoramidite monomer can have the structure

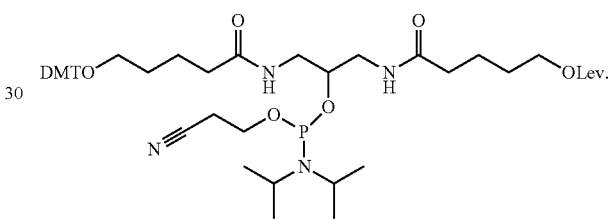

It is noted that the phosphoramidite structure shown at the center of the branching phosphoramidite monomer above is merely exemplary, and any such phosphoramidite structure capable of incorporation into a linear phosphoramidite backbone is considered to be within the present scope.

In another example, the present disclosure provides a comb-like branching molecule that can have the structure

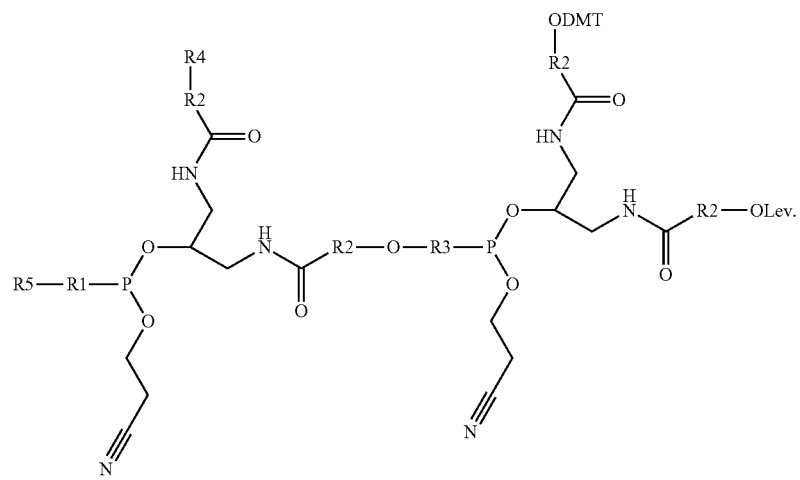

R1 can be a PEG such as —(O—CH$_2$—CH$_2$—)$_n$ where n is 1-5, an alkyl such as —O—(CH$_2$—)$_n$ where n is 1-10, a phosphoramidite, or similar, including combinations thereof. R2 can be a PEG such as —(O—CH$_2$—CH$_2$—)$_n$ where n is 1-5, an alkyl such as —O—(CH$_2$—)$_n$ where n is 1-10, or the like, and R3 can be a spacer. R4 can be an oligonucleotide sequence or other useful sidechain molecular moiety and R5 can be a solid substrate, a reporter molecule, an oligonucleotide, or the like, including combinations thereof.

While the above comb-like branching molecule is shown having two branching phosphoramidite monomers, it is noted that the protected Lev oxygen provides a reactive substrate to add additional branching phosphoramidite monomers. As such, the number of monomers, and therefore orthogonal sidechains, in a comb-like branching molecule is not limiting.

One general example technique for synthesizing a comb-like branching molecule involves adding branching phosphoramidite monomers in series to a growing linear phosphoramidite backbone and synthesizing the sidechain molecule at the time of incorporation of the associated branching phosphoramidite monomer. In other words, a branching phosphoramidite monomer having DMT and Lev protected branches is added to the growing backbone by the monomer's exposed phosphoramidite group. Once the monomer is in place, the DMT protecting group is removed and a sidechain molecule, such as an oligonucleotide, is synthesized from the terminal oxygen moiety of the now exposed monomer branch. Once the sidechain molecule has be synthesized it can be optionally capped to preclude any undesirable reactivity with subsequent chemistry. The Lev protecting group is then removed from the remaining branch of the monomer to expose an oxygen moiety to which the phosphoramidite group of another DMT and Lev protected branching phosphoramidite monomer is coupled.

Figure 3:
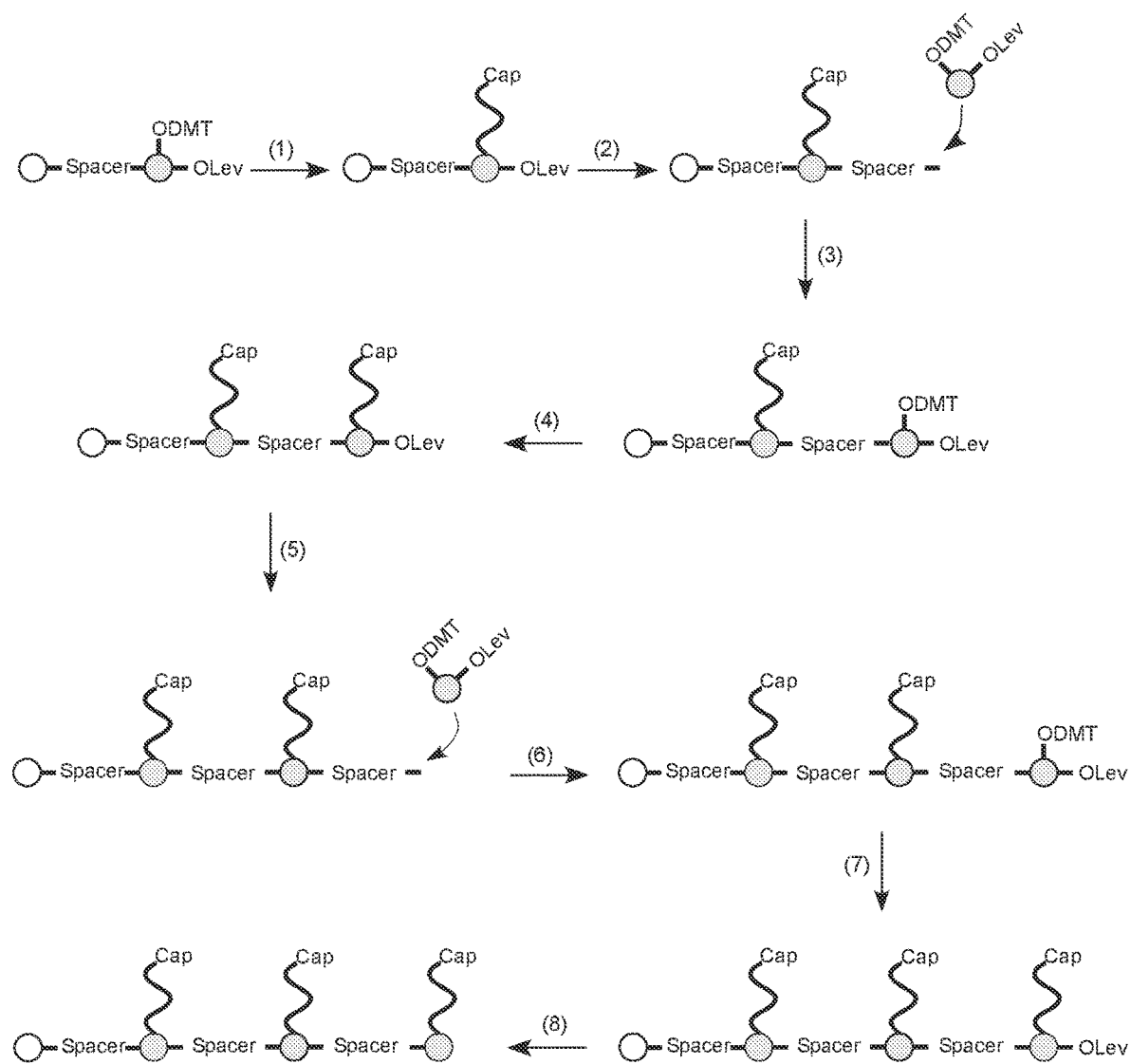
FIG. 3 illustrates a technique for synthesizing a comb-like branching phosphoramidite molecule in accordance with an example of the present disclosure.

FIG. 3 shows one example of such a process in greater detail. In this nonlimiting technique, a spacer is attached to a solid support (e.g. a bead, as shown by the white circle). A first branching phosphoramidite monomer (branching monomer) is coupled to an exposed terminal oxygen moiety (e.g. hydroxyl group) of the spacer. At (1), the protecting DMT is removed by a suitable method, such as using trichloroacetic acid (TCA) for example, followed by sequential coupling of a number of nucleoside phosphoramidites to the now exposed oxygen moiety to generate the first branch of the comb-like molecule. To prevent further elongation, the 5'-hydroxyl of the terminal nucleoside can be capped using acetic anhydride, for example. At (2), the Lev protecting group of the branching monomer is removed using a levulinyl deprotection solution and the exposed hydroxyl group is coupled with a second spacer. In some examples, additional linkers/spacers can be added alter the characteristics of the backbone and/or increase the distance between sidechains. In one example, one or more phosphoramidite species can be added to the spacer. In (3), a second branching monomer is added to the backbone via an exposed hydroxyl group of the second spacer. In (4), the process shown at (1) is repeated to form and cap the second branch of the comb-like molecule. Steps (5), (6), and (7) repeat steps (3), (1), and (2), respectively, resulting in a comb-like molecule with three independently synthesized sidechains. In (8), the remaining Lev group can be removed to add further branching monomers or to terminate growth of the molecule.

Figure 4:
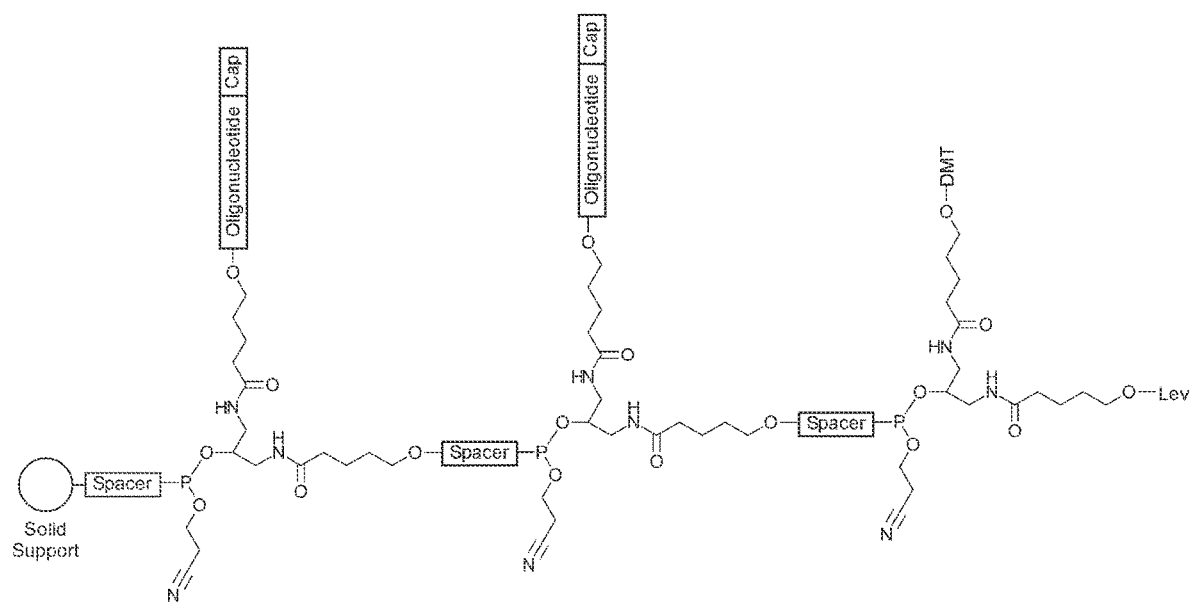
FIG. 4 illustrates a comb-like branching phosphoramidite molecule in accordance with an example of the present disclosure.

FIG. 4 shows one nonlimiting example of a comb-like branching molecule including a spacer coupled to a solid support from which three branching phosphoramidite monomers are coupled in series. The first branching monomer is coupled to an oxygen moiety of the spacer by a phosphate of the phosphoramidite group. The first branching monomer has a first capped oligonucleotide sidechain extending orthogonally from the first branch and a second spacer coupled to the second branch. The second branching monomer is coupled to the second spacer in manner similar to that described for the attachment between the first spacer and the first branching monomer. Similar to the first branching monomer, the second branching monomer has a second capped oligonucleotide sidechain extending orthogonally from the first branch and a third spacer coupled to the second branch. The third branching monomer is coupled to the third spacer in manner similar to that described for the attachment between the first spacer and the first branching monomer. The third branching monomer includes a DMT protecting group on the first branch and a Lev protecting group on the second branch.

In some cases, comb-like branching molecules can be coupled to a solid support (including semisolid supports) to facilitate synthesis as well as use of the molecule. Nonlimiting examples of such can include slides, slide covers, beads, chips, particles, strands, gels, sheets, tubes, spheres, containers, capillaries, pads, slices, films, plates, and the like, including appropriate combinations thereof. Such nonlimiting examples can comprise various materials that can be biologic, nonbiologic, organic, inorganic, natural, synthetic, or a combination thereof. In one example, a solid support can include a bead designed to capture the branched molecule, or a portion thereof, following molecule synthesis, diagnostic, or other use.

Spacers can include any molecular species capable of coupling branching monomers together as described. Spacers can be the same throughout the branching molecule or they may be different at different locations. Additionally, the spacer coupling the branching molecule to a solid support can be the same or different from the spacers coupling branching monomers to one another. In one nonlimiting example, a given spacer can include a PEG spacer, such as —(O—CH$_2$—CH$_2$—)$_n$ where n is 1-5. In another nonlimiting example, a given spacer can include an alkyl, such as —O—(CH$_2$—)$_n$ where n is 1-10. Other examples can include one or more phosphoramidite(s), one or more nucleoside phosphoramidite(s), numerous organic and polymeric molecules known in the art, and the like. Additionally, a given spacer can include a PEG spacer in combination with a nucleoside phosphoramidite, and alkyl spacer in combination with a nucleoside phosphoramidite, or any other suitable combination of known linker molecules. In some examples, a spacer molecule can include a cleavable linker to allow cleavage of the branching molecule from the solid support, to allow portions of the branching molecule to be separated from one another, etc. Such linkers can be cleaved via oxidation/reduction reactions, changes in pH, enzymatic digestion, photo-cleavage, and the like. Furthermore, in some examples barcode sequences can be incorporated into the oligonucleotide sequences, the spacers, or any other portion of the comb-like branching molecule. Such barcode sequences can be positioned identify the comb-like branched molecule as a whole, a section of the comb-like branched molecule, an individual oligonucleotide sequence, a group of oligonucleotide sequences, or the like.

Figure 5A:
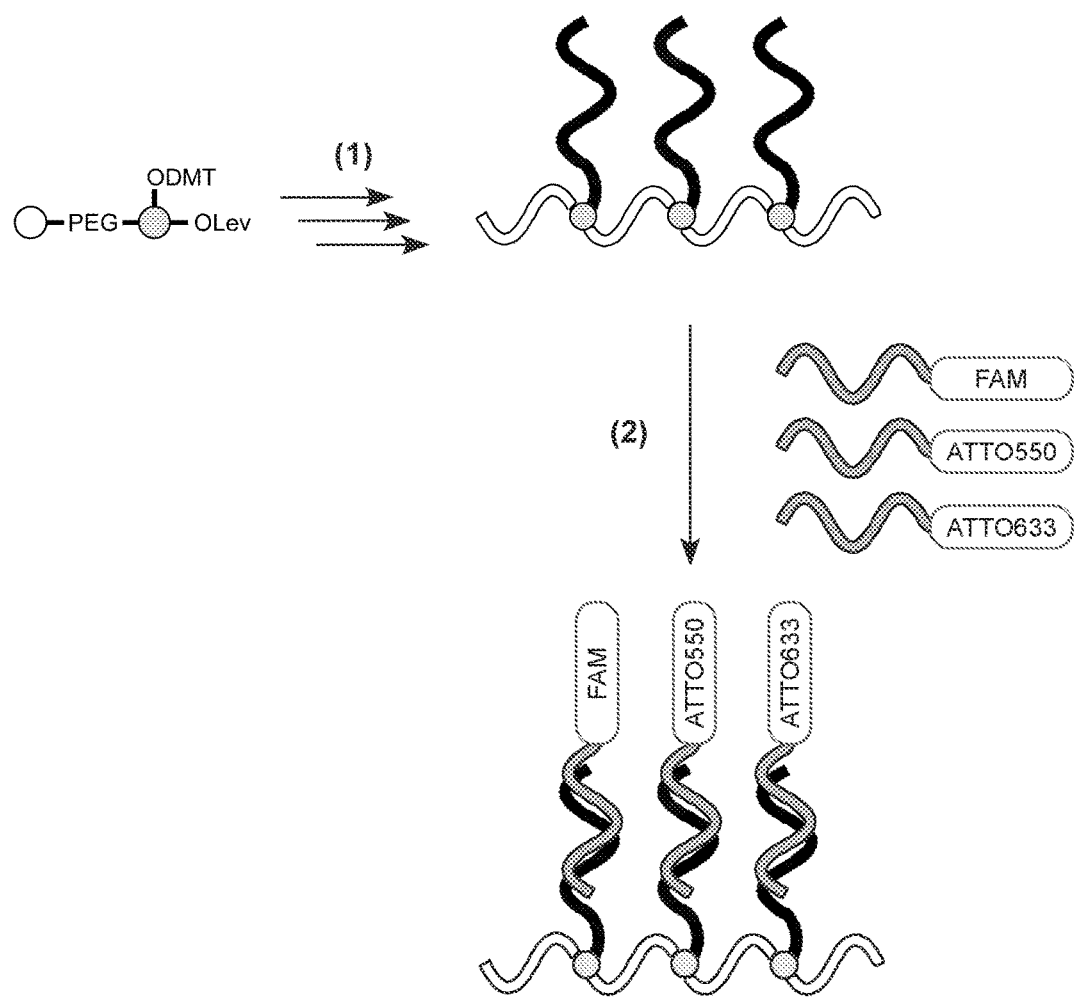
FIG. 5A illustrates a synthesis and validation procedure for a comb-like branching phosphoramidite molecule in accordance with an example of the present disclosure.
Figure 5B:
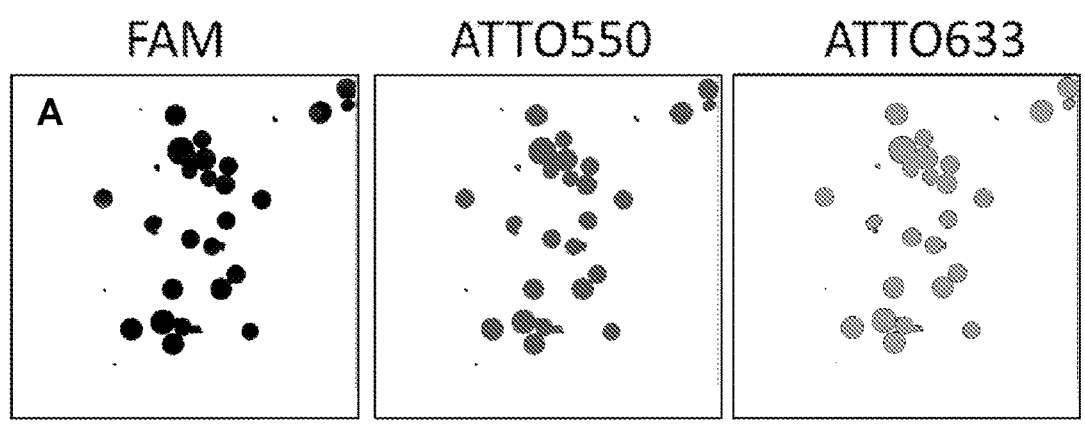
FIG. 5B illustrates data from a synthesis and validation procedure for a comb-like branching phosphoramidite molecule in accordance with an example of the present disclosure.

FIG. 5A shows one nonlimiting example of a diagnostic use for the branching molecules of the present disclosure. Step (1) shows a series of reaction steps to generate a comb-like branching molecule as described above. Three oligonucleotide sidechains are synthesized having three different sequences as shown in Table 1. The branching molecule is kept attached to the solid substrate (not shown), which is mixed in step (2) with fluorescently labeled complementary or mismatched DNA sequences, then visualized using fluorescence microscopy. The beads incubated with complementary DNA probes resulted in bright fluorescence with signals at three different wavelengths, corresponding to successful hybridization to all three bDNA arms, as is shown in FIG. 5B. In contrast, the beads incubated with mismatched DNA probes showed no detectable fluorescence above the background. These results demonstrate both successful synthesis of the bDNA having three different branches and the ability of the DNA arms to hybridize with complementary oligonucleotides when arrayed on the comb scaffold. Such indicates that this readily synthesized branching phosphoramidite will find wide use in the synthesis of b-Oligos for use in biomedical diagnostics, gene-profiling, multicolor imaging, and DNA nanotechnology, to name a few.

EXAMPLES

Examples of various experimental details are described to provide a fuller understanding of the presently disclosed technology and are not intended to be limiting.

Synthesis and Validation of Branched DNA

As shown in FIG. 5A, beads having branched DNA were synthesized using a divergent oligonucleotide synthesis protocol. The beads were coupled with a short PEG spacer phosphoramidite, then the first branching monomer was added. Subsequent deprotection of the DMT group from the branching monomer using trichloroacetic acid (TCA), followed by sequential coupling of 12 nucleoside phosphoramidites, generated the first branch of the bDNA. To prevent further elongation, the 5'-hydroxyl of the terminal nucleoside was capped using acetic anhydride. Next, the Lev group of the branching monomer was removed using levulinyl deprotection solution (0.5 M hydrazine hydrate in 1:1 pyridine:acetic acid, Glen Research) and the hydroxyl group coupled with one PEG, followed by two thymidine phosphoramidites in order to create a spacer between the DNA arms. The second and third branches were synthesized by repeating the same steps to obtain a bDNA having three arms, each with a unique nucleotide sequence (Table 1, SEQ ID NOs: 01-03).

TABLE 1

Sequences of bDNA arms and characterization probes.

| DNA | sequence (5'-3') |
| --- | --- |
| bDNA 1 | ATACCAGATTGT (SEQ ID NO: 01) |
| bDNA 2 | GACAACGATTGC (SEQ ID NO: 02) |
| bDNA 3 | ACTAACGGCTTC (SEQ ID NO: 03) |
| cDNA 4 | ACAATCTGGTAT/FAM (SEQ ID NO: 04) |
| cDNA 5 | GCAATCGTTGTC/Atto550 (SEQ ID NO: 05) |
| cDNA 6 | GAAGCCGTTAGT/Atto633 (SEQ ID NO: 06) |
| mDNA 7 | CTCCGAGAACGC/FAM (SEQ ID NO: 07) |

TABLE 1-continued

Sequences of bDNA arms and characterization probes.

| DNA | sequence (5'-3') |
| --- | --- |
| mDNA 8 | ATGGCTACGGTT/Atto550 (SEQ ID NO: 08) |
| mDNA 9 | TCCATTACGCAC/Atto633 (SEQ ID NO: 09) |

Characterization of bDNAs 1-3 (SEQ ID NOs: 01-03) was achieved using complementary and mismatched probes for each of the DNA arms (Table 1). To enable multiplexed detection, the probes for each arm were equipped with FAM, ATTO550N, or ATTO633N, which have excitation and emission profiles that allow them to be individually imaged using fluorescence microscopy (Table 2).

TABLE 2

Excitation and emission wavelengths of probe fluorophores.

| fluorophore | excitation | emission |
| --- | --- | --- |
| FAM 488 | 495 nm | 520 nm |
| ATTO550N | 560 nm | 575 nm |
| ATTO633N | 635 nm | 653 nm |

Figure 6:
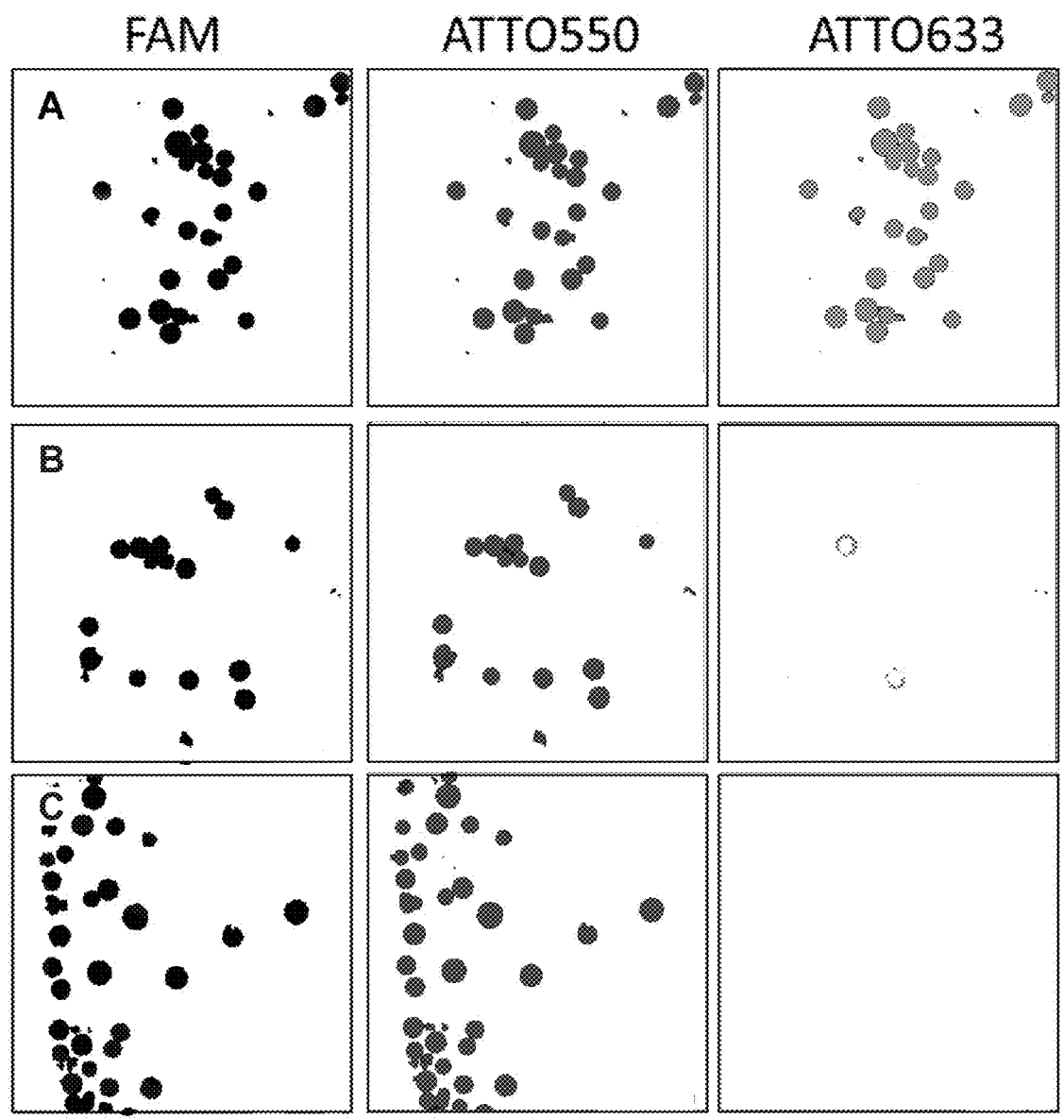
FIG. 6 illustrates data from a synthesis and validation procedure for a comb-like branching phosphoramidite molecule in accordance with an example of the present disclosure.
Figure 7A:
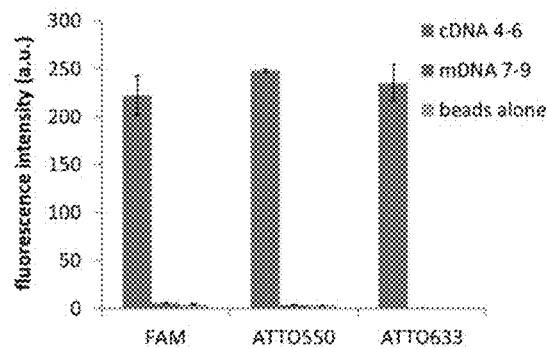
FIG. 7A illustrates data from a synthesis and validation procedure for a comb-like branching phosphoramidite molecule in accordance with an example of the present disclosure.
Figure 7B:
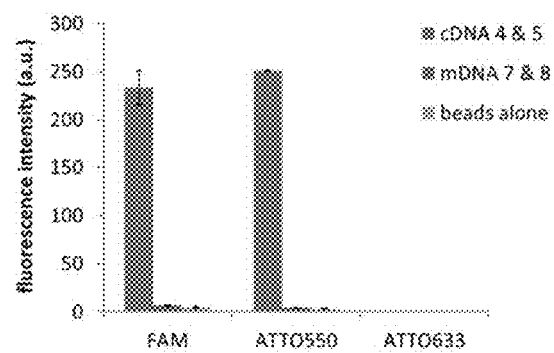
FIG. 7B illustrates data from a synthesis and validation procedure for a comb-like branching phosphoramidite molecule in accordance with an example of the present disclosure.
Figure 7C:
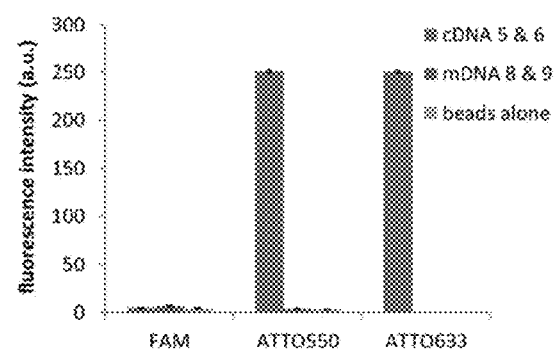
FIG. 7C illustrates data from a synthesis and validation procedure for a comb-like branching phosphoramidite molecule in accordance with an example of the present disclosure.
Figure 7D:
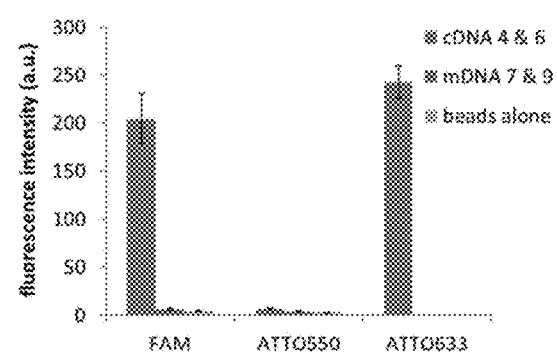
FIG. 7D illustrates data from a synthesis and validation procedure for a comb-like branching phosphoramidite molecule in accordance with an example of the present disclosure.

The bDNA-functionalized beads were incubated with all possible combinations of cDNA or mDNA probes (5.0 µM in 1× PBS with 0.1% tween). The samples were heated to 90° C. for 5 min, then cooled to room temperature and the excess unhybridized DNA removed by washing with PBS. The samples were transferred into a 96-well plate and imaged using confocal microscopy. The beads incubated with all three complementary DNA probes (cDNA 4-6, SEQ ID NOs: 04-06) showed bright fluorescence in the blue (dark, left column), green (medium, middle column), and red (light, right column) imaging channels corresponding to the fluorophores appended to the probes (FIG. 6, row A). In comparison, fluorescence images obtained for beads incubated with all three mismatch DNA probes (mDNA 7-9, SEQ ID NOs: 07-09) showed only faint signal (FIG. 6, row B), and were comparable to the background fluorescence intensity observed for beads alone (FIG. 6, row C). FIG. 6 shows a color-altered drawing of confocal images of bDNA-functionalized beads. Row A shows bDNA beads incubated with complementary DNA probes cDNA 4-6 (SEQ ID NOs: 04-06); Row B shows bDNA beads incubated with mismatched DNA probes mDNA 7-9 (SEQ ID NOs: 07-09); and Row C shows background fluorescence signal of bDNA beads alone.

Fluorescence intensities were quantitatively assessed by analyzing images of 10-individual beads from each sample using ImageJ software. In agreement with the images shown in FIG. 3, the beads incubated with all three complementary DNA probes showed high fluorescence intensities in all channels, whereas beads incubated with all three mismatch DNA probes showed low fluorescence intensities in all channels, and these were comparable to the background fluorescence intensities observed for the bDNA beads alone (FIG. 7, panel A). To further validate the selectivity of bDNA hybridization, we imaged beads incubated with all possible combinations of two different probes. As shown in FIG. 7, panels B-D, these experiments yielded the anticipated result of observing fluorescence in only two channels when using two complementary probes, and observing only background fluorescence when using mismatched probes. Together, these data indicate that our branching monomer enabled the synthesis of bDNA having three different sequence arms, and that each of the arms can be selectively hybridized to a complementary oligonucleotide.

FIG. 7 shows fluorescence intensities quantified from confocal microscopy images. Panel A shows bDNA beads incubated with cDNAs 4-6 (SEQ ID NOs: 04-06) or mDNAs 7-9 (SEQ ID NOs: 07-09); Panel B shows bDNA beads incubated with cDNAs 4 & 5 (SEQ ID NOs: 04 & 05) or mDNAs 7 & 8 (SEQ ID NOs: 07 & 08); Panel C shows bDNA beads incubated with cDNAs 5 & 6 (SEQ ID NOs: 05 & 06) or mDNAs 8 & 9 (SEQ ID NOs: 08 & 09); and Panel D shows bDNA beads incubated with cDNAs 4 & 6 (SEQ ID NOs: 04 & 06) or mDNAs 7 & 9 (SEQ ID NOs: 07 & 09). Background fluorescence for bDNA beads and some mDNAs was not detectable in ATTO633 channel.

It is thus shown a facile route for the synthesis of a non-nucleosidic branching phosphoramidite having orthogonal DMT and Lev protecting groups. The branching unit can be utilized in solid-phase oligonucleotide synthesis to generate a comb-shaped DNA having multiple arms with different DNA sequences. We initially synthesized a bDNA having three arms, but the oligonucleotide synthesis strategy could be easily iterated to generate comb-shaped DNAs having several more arm units appended. Characterization by fluorescence imaging revealed successful synthesis of the bDNA and selective hybridization of complementary oligonucleotide probes to each arm. While previous approaches to covalently linked bDNAs were hindered by the challenging synthesis of asymmetrically-protected branching monomers, the relative ease of our approach is anticipated to facilitate the synthesis of these biomolecular architectures. This is in turn anticipated to drive the development of new technologies in diagnostics, imaging, and nanotechnology.

Synthesis of Branching Monomer

Figure 8:
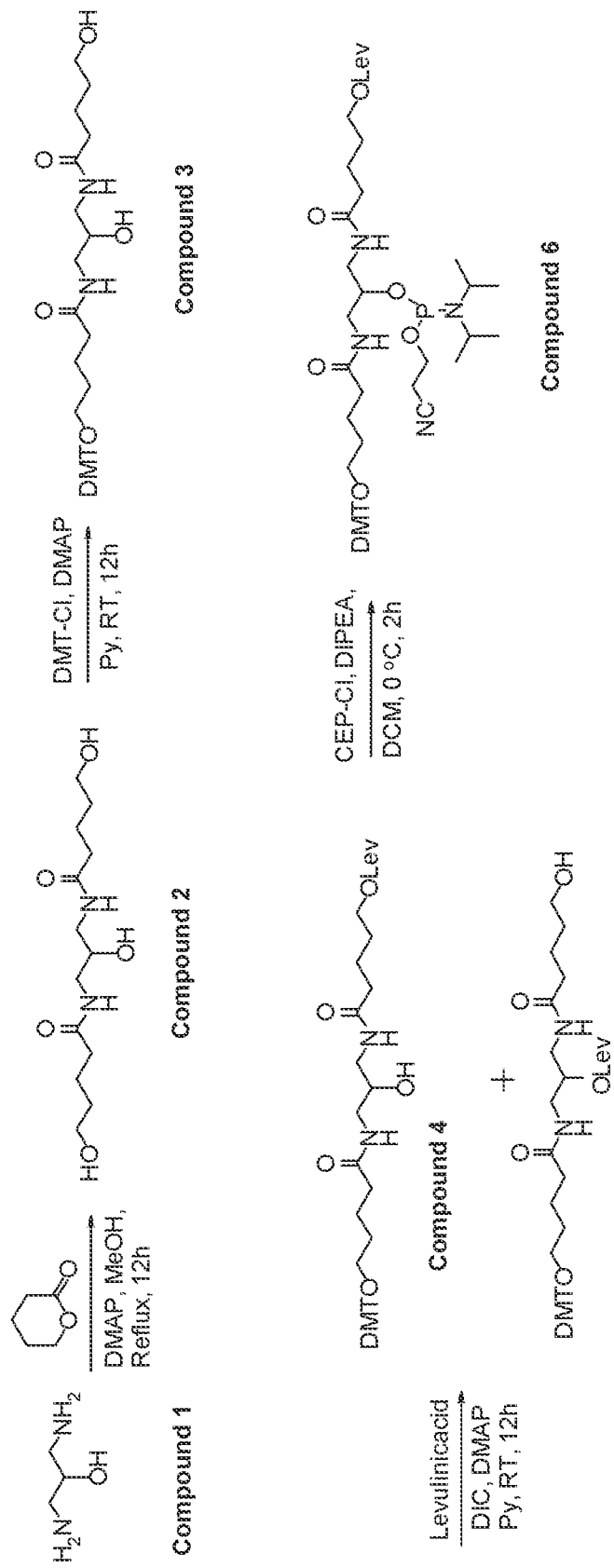
FIG. 8 illustrates a technique for synthesizing a branching phosphoramidite monomer in accordance with an example of the present disclosure.

As is shown in FIG. 8, synthesis of branching monomer (6) was initiated by refluxing commercially available 1,3-diaminopropan-2-ol (1) with δ-velarolactone to obtain (2), having eight-atom arms to reduce steric congestion upon bDNA synthesis. Monoprotection of triol (2) with a DMT group was achieved by treatment with DMT-Cl in pyridine. DMT-protected (3) was then treated with levulinic acid under ester bond forming conditions (DIC/DMAP) to obtain orthogonally-protected levulinate esters (4) and (5). The desired compound (4) was isolated and treated with CEP-Cl to yield branching phosphoramidite monomer (6). Further detailed synthesis of compounds 2-6 is presented in the following examples.

Synthesis of N,N'-(2-hydroxypropane-1,3-diyl)bis(5-hydroxypentanamide) (Compound 2).

To a solution of 1,3-diaminopropan-2-ol (compound 1) (3.5 g, 38.88 mmol) in methanol (25.0 mL), 4-(dimethylamino)pyridine (DMAP) (190.0 mg, 1.55 mmol) and δ-valerolactone (7.9 mL, 85.55 mmol) were added at room temperature. The mixture was refluxed for 12 h. After completion of the reaction, the solvent was removed in vacuo and the product was precipitated from 25.0 mL of dicholormethane at 4° C. to give compound 2 as a white powder. Yield 9.0 g, 79%. $^1$H NMR (300 MHz, $CD_3OD$) δ 1.55-1.68 (m, 8H), 1.22-2.35 (m, 4H), 3.21-3.24 (m, 4H), 3.54-3.58 (m, 4H), 3.71 (t, 1H, J=6 Hz); $^{13}$C NMR (75 MHz, $CD_3OD$) δ 16.7, 21.3, 22.2, 31.8, 31.9, 33.3, 35.6, 42.9, 61.2, 61.3, 69.1, 175.3; LRMS (ESI-TOF) m/z Calcd for $C_{13}H_{25}N_2O_5$ [M +Na]$^+$313.17; Found 313.17

Synthesis of 5-(bis(4-methoxyphenyl)(phenyl)methoxy)-N-(2-hydroxy-3-(5-hydroxypentanamido)propyl)pentanamide (Compound 3).

To a solution of compound 2 (4.0 g, 13.79 mmol) in pyridine (25.0 mL), DMAP (670.0 mg, 5.52 mmol) and DMT-Cl (4.7 g, 13.79 mmol) were added at room temperature and the reaction mixture stirred for 12 h. After completion of the reaction, the solvent was removed in vacuo and the product was purified using column chromatography (10% MeOH:DCM). Yield 3.0 g, 37%. $^1$H NMR (300 MHz, $CDCl_3$) δ 1.53-1.71 (m, 8H), 2.15-2.25 (m, 4H), 3.04 (t, 2H, J=3 Hz), 3.14-3.33 (m, 4H), 3.43 (bs, 1H), 3.58-3.60 (m, 2H), 3.69-3.71(m, 1H), 3.75 (s, 6H), 4.83 (bs, 1H), 6.78-6.81 (m, 4H), 7.27-7.39 (m, 9H); $^{13}$C NMR (75 MHz, $CDCl_3$) δ 22.1, 22.8, 29.8, 32.0, 36.1, 36.5, 42.6, 55.4, 62.1, 63.1, 86.0, 113.2, 126.9, 127.9, 128.4, 130.2, 136.7, 145.4, 158.5, 175.2. LRMS (ESI-TOF) m/z Calcd for $C_{34}H_{44}N_2NaO_7$ [M +Na]$^+$615.30; Found 615.4.

5-((3-(5-(bis(4-methoxyphenyl)(phenyl)methoxy)pentanamido)-2-hydroxypropyl)amino)-5-oxopentyl 4-oxopentanoate (Compound 4).

To a solution of compound 3 (3.0 g, 5.07 mmol) in pyridine (25.0 mL), DMAP (620.0 mg, 5.07 mmol), DIC (1.4 mL, 10.14 mmol) and levulinic acid (880.0 mg, 7.60 mmol) were added at room temperature and the reaction mixture stirred for 12 h. After completion of the reaction, the solvent was removed in vacuo and the product was extracted with dichloromethane (3×25 mL). The organic layer was dried over anhydrous $Na_2SO_4$ and purified using column chromatography (2% MeOH:DCM) to obtain compound 4. Yield 1.4 g, 40%. $^1$H NMR (300 MHz, $CDCl_3$) δ 1.65-1.72 (m, 8H), 2.16-2.27 (m, 7H), 2.55 (t, 2H, J=6 Hz), 2.75 (t, 2H, J=6 Hz), 3.07 (t, 2H, J=6 Hz), 3.21-3.38 (m, 4H), 3.72-3.75 (m, 1H), 3.79 (s, 6H), 4.10 (t, 2H, J=6 Hz), 6.26 (bs, 1H), 6.49 (bs, 1H), 6.82 (d, 4H, J=9 Hz), 7.19-7.32 (m, 7H), 7.42 (d, 2H, J=6 Hz); $^{13}$C NMR (75 MHz, $CDCl_3$) δ 22.2, 22.6, 27.9, 35.8, 36.3, 38.0, 55.2, 62.8, 64.0, 113.0, 126.6, 127.7, 128.2, 129.2, 130.0, 136.5, 158.3; LRMS (ESI-TOF) m/z Calcd for $C_{39}H_{49}N_2O_9$ [M-H]$^+$689.34; Found 689.0.

1-(5-(bis(4-methoxyphenyl)(phenyl)methoxy)pentanamido)-3-(5-hydroxypentanamido)propan-2-yl 4-oxopentanoate (Compound 5).

$^1$H NMR (300 MHz, $CDCl_3$) δ 1.57-1.72 (m, 8H), 2.13 (s, 3H), 2.16-2.28 (m, 4H), 2.45 (t, 2H, J=6 Hz), 2.74-2.79 (m, 2H), 3.05 (t, 2H, J=6 Hz), 3.24-3.34 (m, 2H), 3.43-3.55 (m, 2H), 3.58-3.63 (m, 2H), 3.76 (s, 6H),4.79-4.84 (m, 1H), 6.55 (bs, 1H), 6.80 (d, 4H, J=6 Hz), 7.17-7.31 (m, 7H), 7.41 (d, 2H, J=6 Hz); $^{13}$C NMR (75 MHz, $CDCl_3$) δ 22.0, 22.9, 28.4, 29.9, 30.0, 32.2, 36.2, 36.7, 38.7, 38.8, 38.9, 55.4, 62.2, 63.1, 71.8, 86.0, 113.2, 126.8, 127.9, 128.4, 130.2, 136.8, 145.5, 158.5, 172.3, 174.3. LRMS (ESI-TOF) m/z Calcd for $C_{39}H_{49}N_2O_9$ [M-H]$^+$689.34; Found 689.2.

5-((3-(5-(bis(4-methoxyphenyl)(phenyl)methoxy)pentanamido)-2-(((2-cyanoethoxy)(diisopropylamino)phosphaneyl)oxy)propyl)amino)-5-oxopentyl 4-oxopentanoate (Compound 6).

To a solution of compound 4 (500.0 mg, 0.72 mmol) in dichloromethane (25.0 mL), DIPEA (0.5 mL, 2.89 mmol) and 2-cyanoethyl N,N-diisopropylchlorophosphoramidite (CEP-Cl, 0.16 mL, 0.79 mmol) were added at 0° C. and stirred at room temperature for 2 h. After completion of the reaction, the mixture was diluted with dichloromethane and washed with aqueous $NaHCO_3$ solution. The organic layer was dried over anhydrous Na2SO$_4$ and purified on neutralized silica (silica gel was stirred in trimethylamine and hexane for 1 h) and the product was eluted with 2% MeOH:DCM to obtain compound 6 as a semi-solid. Yield 300.0 mg, 46%. $^1$HNMR (300 MHz, $CDCl_3$) δ 1.12-1.21 (m, 16H), 1.66-1.70 (m, 8H), 2.18-2.25 (m, 6H), 2.55-2.74 (m, 5H), 3.05-3.07(m, 3H), 3.60-3.85 (m, 12 H), 4.06 (t, 2H, J=6 Hz), 6.38-6.57 (m, 2H), 6.80 (d, 4H, J=9 Hz), 7.26-7.32 (m, 8H); $^{13}$C NMR (75 MHz, $CDCl_3$) δ 20.6, 22.1, 22.2, 22.7, 23.5, 24.6, 24.7, 27.9, 28.1, 29.7, 29.9, 35.9, 36.0, 36.5, 36.6, 37.9, 40.5, 42.2, 43.1, 43.3, 55.2, 58.1, 58.4, 62.9, 64.2, 70.6, 70.8, 85.7, 112.9, 126.5, 127.7, 128.1, 130.0, 136.6, 145.3, 158.3, 172.7, 173.6; $^{31}$P NMR (121.5 MHz, CDCl$_3$, H$_3$PO$_4$ as external reference) δ 148.18. LRMS (ESI-TOF) m/z Calcd for C$_{48}$H$_{67}$N$_4$NaO$_{10}$P [M+Na]$^+$913.45; Found 913.6.

Fluorescence Bead Imaging.

bDNA bead samples for confocal imaging were prepared having a concentration of 5.0 µM of each complementary or mismatched DNA probe in 1× PBS with 0.1% tween. Each sample was heated to 90° C. for 5 min, then slowly cooled to room temperature. The excess unhybridized DNA probe solution was removed carefully and the beads washed three times with 1× PBS. For each sample, 100 µL of 1× PBS was added and the beads were transferred to a 96-well plate. The samples were imaged on a Leica DMi8 confocal fluorescence microscope with a 10× objective using the following settings: FAM, 488 nm excitation (1.04% laser intensity), 593-556 nm emission (band-pass); Atto550, 561 nm excitation (67.1% laser intensity), 566-628 nm emission (band pass); Atto633, 633 nm excitation (35.5% laser intensity), 638-783 nm emission (band-pass). The confocal settings for all samples were kept constant throughout the experiment. The fluorescence intensities were acquired from confocal images by averaging the fluorescence intensities of 10 individual beads from each image using ImageJ software.

While the forgoing examples are illustrative of the principles of various embodiments in one or more particular applications, it will be apparent to those of ordinary skill in the art that numerous modifications in form, usage and details of implementation can be made without the exercise of inventive faculty, and without departing from the principles and concepts of the disclosure.

What is claimed is:

1. A branching phosphoramidite monomer having the structure

[Structure: DMTO-(CH2)3-C(=O)-NH-CH2-CH(O-P(OCH2CH2CN)(N(iPr)2))-CH2-NH-C(=O)-(CH2)3-OLev]

2. A method of making a comb-type branching molecule, comprising:
   acquiring a substrate having an attached substrate linker with an exposed hydroxyl group;
   acquiring a first branching phosphoramidite (PA) monomer having dimethoxytrityl (DMT) protection at $O^a$, levulinyl (Lev) protection at $O^b$, and a PA group according to structure (I)

(I)

[Structure: $DMTO^a$-(CH2)3-C(=O)-NH-CH2-CH(O-PA)-CH2-NH-C(=O)-(CH2)3-$O^b$Lev]

bonding the hydroxyl group of the substrate linker to the PA group;
   removing the DMT protection from the $O^a$ of the first branching PA monomer;
   generating a first oligonucleotide sequence extending from the $O^a$ of the first branching PA monomer;
   removing the Lev protection from the $O^b$ of the first branching PA monomer;

bonding the $O^b$ of the first branching PA monomer to the PA group of a second branching PA monomer having the structure (I);

removing the DMT protection from the $O^a$ of the second branching PA monomer;

generating a second oligonucleotide sequence extending from the $O^a$ of the second branching PA monomer;

removing the Lev protection from the $O^b$ of the second branching PA monomer; and bonding the $O^b$ of the second branching PA monomer to the PA group of a third branching PA monomer having the structure (I).

3. The method of claim 2, wherein bonding the $O^b$ of the first or second branching PA monomer to the PA group of the second or third branching PA monomer further comprises:

bonding the $O^b$ of the first or second branching PA monomer to a linear spacer molecule having a terminal hydroxyl group; and bonding the terminal hydroxyl group of the linear spacer to the PA group of the second or third branching PA monomer.

4. The method of claim 2, wherein removing the Lev protection from the $O^b$ of the first branching PA monomer or the second branching PA monomer further comprises capping the first oligonucleotide sequence or the second oligonucleotide sequence prior to removing the Lev protection.

5. The method of claim 2, further comprising cleaving the first branching PA monomer from the substrate.

6. The method of claim 2, further comprising adding one or more additional branching PA monomers to the comb-type branching molecule by repeating the steps of claim 2.

* * * * *

SEQUENCE LISTING

```
<160> NUMBER OF SEQ ID NOS: 9

<210> SEQ ID NO 1
<211> LENGTH: 12
<212> TYPE: DNA
<213> ORGANISM: Artificial Sequence
<220> FEATURE:
<223> OTHER INFORMATION: Completely Synthesized

<400> SEQUENCE: 1
ataccagatt gt                                                         12

<210> SEQ ID NO 2
<211> LENGTH: 12
<212> TYPE: DNA
<213> ORGANISM: Artificial Sequence
<220> FEATURE:
<223> OTHER INFORMATION: Completely Synthesized

<400> SEQUENCE: 2
gacaacgatt gc                                                         12

<210> SEQ ID NO 3
<211> LENGTH: 12
<212> TYPE: DNA
<213> ORGANISM: Artificial Sequence
<220> FEATURE:
<223> OTHER INFORMATION: Completely Synthesized

<400> SEQUENCE: 3
actaacggct tc                                                         12

<210> SEQ ID NO 4
<211> LENGTH: 12
<212> TYPE: DNA
<213> ORGANISM: Artificial Sequence
<220> FEATURE:
<223> OTHER INFORMATION: Completely Synthesized

<400> SEQUENCE: 4
acaatctggt at                                                         12

<210> SEQ ID NO 5
<211> LENGTH: 12
<212> TYPE: DNA
<213> ORGANISM: Artificial Sequence
<220> FEATURE:
<223> OTHER INFORMATION: Completely Synthesized
```

```
<400> SEQUENCE: 5
gcaatcgttg tc                                                              12

<210> SEQ ID NO 6
<211> LENGTH: 12
<212> TYPE: DNA
<213> ORGANISM: Artificial Sequence
<220> FEATURE:
<223> OTHER INFORMATION: Completely Synthesized

<400> SEQUENCE: 6
gaagccgtta gt                                                              12

<210> SEQ ID NO 7
<211> LENGTH: 12
<212> TYPE: DNA
<213> ORGANISM: Artificial Sequence
<220> FEATURE:
<223> OTHER INFORMATION: Completely Synthesized

<400> SEQUENCE: 7
ctccgagaac gc                                                              12

<210> SEQ ID NO 8
<211> LENGTH: 12
<212> TYPE: DNA
<213> ORGANISM: Artificial Sequence
<220> FEATURE:
<223> OTHER INFORMATION: Completely Synthesized

<400> SEQUENCE: 8
atggctacgg tt                                                              12

<210> SEQ ID NO 9
<211> LENGTH: 12
<212> TYPE: DNA
<213> ORGANISM: Artificial Sequence
<220> FEATURE:
<223> OTHER INFORMATION: Completely Synthesized

<400> SEQUENCE: 9
tccattacgc ac                                                              12
```